United States Patent [19]

Hefner, Jr.

[11] Patent Number: 4,544,704
[45] Date of Patent: * Oct. 1, 1985

[54] POLYMERIC CYANATE COMPOSITIONS

[75] Inventor: Robert E. Hefner, Jr., Lake Jackson, Tex.

[73] Assignee: The Dow Chemical Company, Midland, Mich.

[ * ] Notice: The portion of the term of this patent subsequent to Oct. 16, 2001 has been disclaimed.

[21] Appl. No.: 578,927

[22] Filed: Feb. 10, 1984

Related U.S. Application Data

[63] Continuation-in-part of Ser. No. 517,560, Jul. 27, 1983, abandoned.

[51] Int. Cl.$^4$ .................. C07C 122/00; C08G 61/02; C08L 65/00; C08L 63/00

[52] U.S. Cl. .................. 525/108; 525/328.2; 525/374; 525/529; 525/113

[58] Field of Search .................. 525/108, 529, 328.2, 525/374

[56] References Cited

U.S. PATENT DOCUMENTS 4,477,629  10/1984  Hefner .................. 525/113

Primary Examiner—John C. Bleutge
Assistant Examiner—A. L. Carrillo
Attorney, Agent, or Firm—J. G. Carter

[57] ABSTRACT

New compositions of matter are disclosed which comprise (1) a copolymer of an ethylenically unsaturated aromatic cyanate and a polymerizable ethylenically unsaturated compound which is free of cyanate groups or mixture thereof, (2) optionally a polycyanate or mixture thereof and/or (3) an epoxy resin.

46 Claims, No Drawings

POLYMERIC CYANATE COMPOSITIONS

CROSS REFERENCE TO RELATED APPLICATION

This is a continuation-in-part of copending application Ser. No. 517,560 filed July 27, 1983 now abd.

BACKGROUND OF THE INVENTION

The present invention pertains to novel thermosettable polymeric cyanates.

Thermosettable aromatic or bridged aromatic cyanates and the polytriazines resulting from curing of said cyanates are known in the prior art, for example, as taught by German Pat. Nos. 1,190,184; 1,195,764; and 1,720,740. In U.S. Pat. No. 3,694,410, a variety of polymeric dicyanates of the structure NC—O—R—O—CN with R being an oligomeric chain of bridged aromatic nuclei are taught. These dicyanates, however, suffer in reactivity upon curing due to the presence of the large bridging (R group) structures which inherently lower the density of curable cyanate groups. Further, the properties of these cured compositions become largely dependent upon said bridging (R group) structures rather than the polytriazine functionality, per se. As is emphasized in U.S. Pat. No. 4,094,852, the moisture sensitivity of the prior art polytriazines is unacceptably high.

A co-pending application by Robert E. Hefner, Jr. entitled "Poly(Cyanato)Poly(Alkenyl Phenol) Compositions" teaches the preparation and curing of novel poly(cyanato)poly(alkenyl phenol) compositions. Said compositions provide cured products with excellent overall properties, however, for the preparation of poly(cyanato)poly(alkenyl phenol)homopolymers, it would be desirable to reduce the number of cyanate groups within the poly(alkenyl phenol) chains without leaving free phenolic hydroxyl groups which are capable of decreasing moisture resistance.

The present invention provides polymeric cyanates of high reactivity and useful cured compositions via homopolymerization to the polytriazines. Polymeric cyanate compositions containing controlled numbers of cyanate groups within the polymer chains are obtained without the penalty of leaving unreacted free phenolic hydroxyl groups. Copolymerization of these polymeric cyanates with difunctional cyanates of the prior art provides polytriazines with improved mechanical properties and reduced moisture sensitivity. Copolymerization of these polymeric cyanates with epoxy resins provides useful cured compositions containing both triazine and oxazoline structures. These resins are useful in the preparation of laminates, castings, coatings and the like.

SUMMARY OF THE INVENTION

The present invention concerns a composition which comprises:
(A) from about 1 to 100, preferably from about 1 to about 80, most preferably from about 10 to about 50, percent by weight (pbw) of a polymeric cyanate or mixture of polymeric cyanates represented by the formula

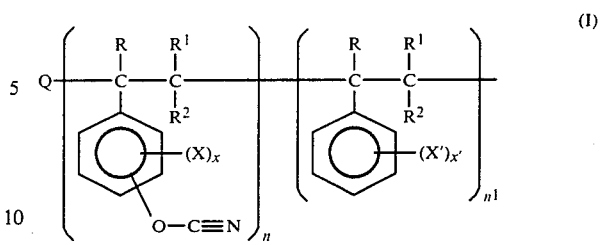

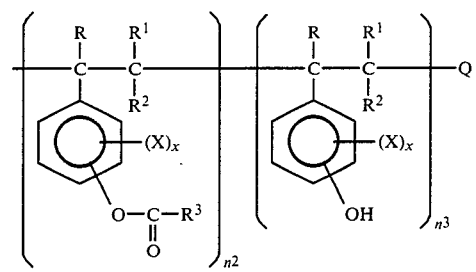

wherein each R, $R^1$ and $R^2$ is independently hydrogen or an alkyl group having from 1 to about 3 carbon atoms; $R^3$ is an alkyl group having from 1 to about 3 carbon atoms; each X and X' is independently an alkyl group having from 1 to about 4 carbon atoms, chlorine or bromine; Q is independently a group derived from any suitable polymerization initiator or terminator, hydrogen,

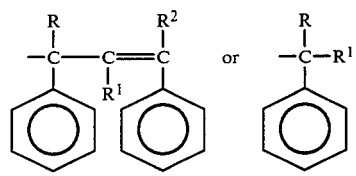

and wherein each aromatic ring may contain any substituent group as those enumerated in the formula I; n has a value of from about 1 to about 5000, preferably from about 10 to about 2500; $n^1$ has a value from about 1 to about 5000, preferably from about 100 to about 3000; $n^2$ has a value of from about zero to about 1000, preferably zero; $n^3$ has a value from about zero to about 1000, preferably zero; and each x and x' independently has a value from zero to 4; and
(B) from zero to about 99, preferably from about 5 to about 70, most preferably from about 25 to about 50, pbw of an aromatic polycyanate or mixture of aromatic polycyanates represented by the formula:

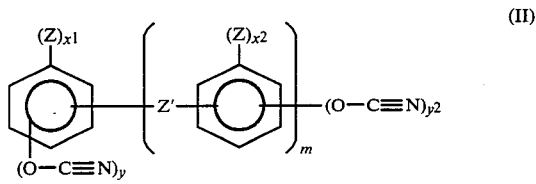

wherein each Z is independently hydrogen, an alkyl group having from 1 to about 4 carbon atoms, chlorine, bromine, or a

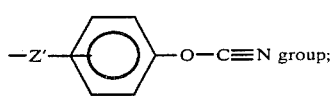

Z' is a direct bond, an alkylene group with 1 to 5 carbon atoms, —S—, —S—S—, —O—,

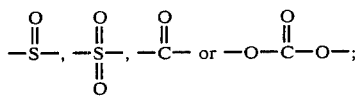

y has a value from zero to 5 when m has a value of 1 to 3; y has a value from 2 to 5 when m has a value of zero; $x^1$ has a value of 5 minus the value of y when m has a value of 1 to 3; $x^1$ has a value of 6 minus the value of y plus $y^2$ when m has a value of zero; $x^2$ has a value of 5 minus the value of $y^2$; $y^2$ has a value of zero to 5; m has a value of zero to 3; with the proviso that the sum of y and $y^2$ is always at least two; and (C) from zero to about 99, preferably from about one to about 50, most preferably from five to about 25, pbw of an epoxy resin or mixture of epoxy resins represented by the formulas

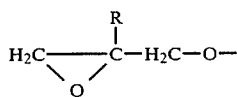
III

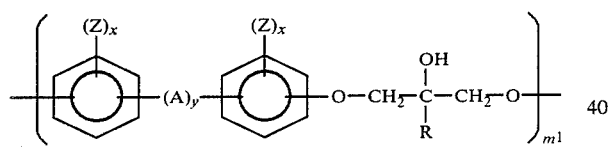

or

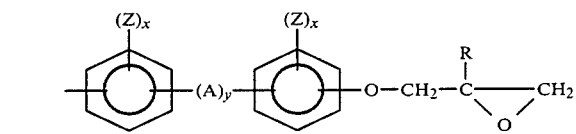

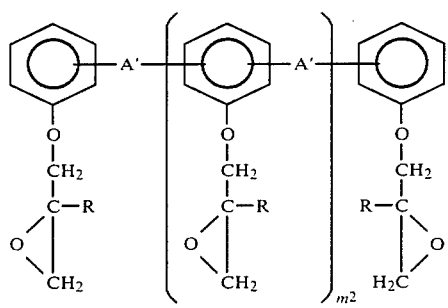

wherein R, Z and x are as hereinbefore defined; each A is independently a hydrocarbyl group having from 1 to about 10, preferably from about 1 to about 4 carbon atoms, —S—, —S—S—, —O—,

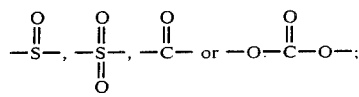

each $A^1$ is independently a hydrocarbyl group having from 1 to about 10, preferably from 1 to about 4 carbon atoms, each y independently has a value of zero or 1; $m^1$ has a value of zero to about 99, preferably from about zero to 5; $m^2$ has a value of 1 to 10 and wherein the pbw of the individual components is based upon total composition.

DETAILED DESCRIPTION OF THE INVENTION

The polymeric cyanates employed herein which are represented by formula I are prepared from a copolymer of a styrene and an alkenylphenyl ester represented by formula V which has been partially hydrolyzed to provide a polymer containing styrene, alkenylphenyl ester and alkenylphenol units represented by formula VI or totally hydrolyzed to provide a polymer containing styrene and alkenylphenol units represented by formula VII.

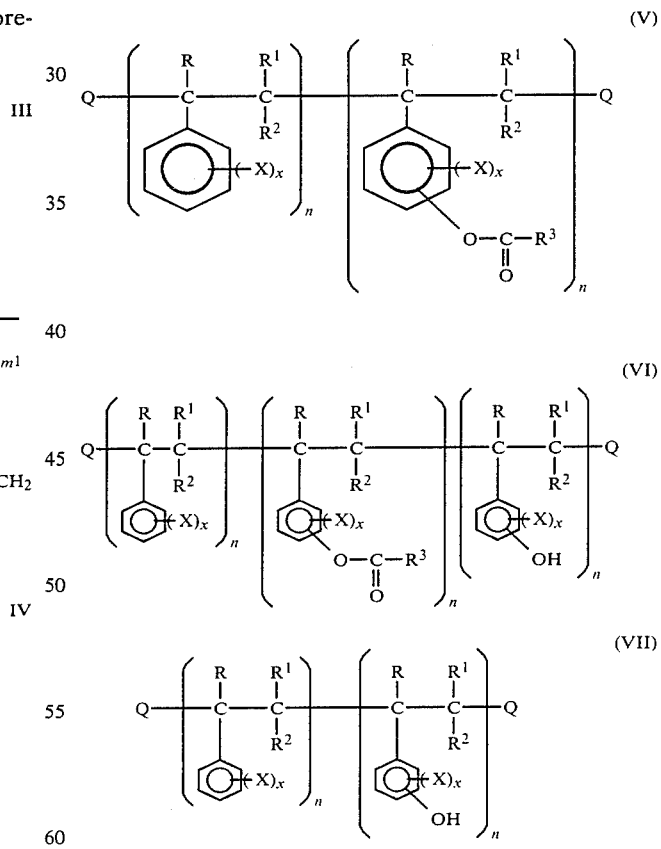

wherein R, $R^1$, $R^2$, $R^3$, X, Q, n and x are as hereinbefore defined. The polymeric cyanates which are repesented by formula I where $n^2$ is zero can be prepared by the reaction of less than the stoichiometric equivalent of a cyanogen halide and the corresponding less than stoichiometric base per hydroxyl group with totally hydrolyzed copolymer of a styrene and an alkenylphenyl ester (formula VII). The polymeric cyanates which are represented by formula I where $n^3$ is zero can be prepared by the reaction of stoichiometric or slight stoichiometric excess (up to about 20 percent) of a cyanogen halide and stoichiometric base per hydroxyl group with partially hydrolyzed copolymer of a styrene and an alkenylphenyl ester (formula VI). The polymeric cyanates which are represented by formula I, where $n^2$ and $n^3$ are both zero, can be prepared by the reaction of stoichiometric or slight stoichiometric excess (up to about 20 percent) of a cyanogen halide and stoichiometric base per hydroxyl group with totally hydrolyzed copolymer of a styrene and an alkenylphenyl ester represented by formula VII. Suitable cyanogen halides include cyanogen bromide and cyanogen chloride. Alternately, the method of Martin and Bauer described in *Organic Synthesis,* Volume 61, pp. 35–68 (1983) and published by John Wiley and Sons can be used to generate the required cyanogen halide is situ from sodium cyanide and a halogen such as chlorine or bromine. Suitable bases include both inorganic bases and tertiary amines such as sodium hydroxide, potassium hydroxide, triethylamine, and the like. Suitable solvents include water, acetone, chlorinated hydrocarbons, ketones and the like. Reaction temperatures of from about −40° to about 60° C. are operable with temperatures of −20° to 25° C. being preferred.

The average molecular weights of the polymeric cyanates vary as a function of the average molecular weight of the respective copolymer of a styrene and an alkenylphenyl ester precursor as well as the extent of hydrolysis and the extent of cyanation. The extent of cyanation may be varied such that each phenolic nucleus within the polymer chains is converted to a cyanate group (formula I wherein $n^3$ is zero) or only a portion of said phenolic hydroxyl groups are converted to cyanate groups (formula I wherein $n^3$ has a value of 1 to about 1000).

In those instances where X is a halogen or an alkyl group, such products can be prepared by halogenating or alkylating the aromatic ring of the copolymer of a styrene and an alkenylphenyl ester prior to use in a cyanation reaction. Alternately, the halogen or alkyl groups can be incorporated into the copolymer by direct copolymerization of monomers containing said group(s). As a specific example, chlorostyrene and an alkenylphenyl ester can be copolymerized to provide suitable copolymer precursor wherein X is chlorine and, furthermore, X is specifically present only on the styrene aromatic rings within the polymer chains. Useful products are prepared wherein all, a part, or none of the aromatic rings simultaneously bear halogen or alkyl groups. Said products, wherein X is a halogen, are useful intermediates for fire retardant polymers.

The copolymer of a styrene and an alkenylphenyl ester starting material(s) can be prepared by polymerizing an alkenylphenyl ester or mixture of alkenylphenyl esters and a styrene or mixture of styrenes by any suitable means such as heating in the presence or absence of a catalyst in the presence or absence of a solvent at a temperature of from about 25° C. to about 150° C. A most preferred catalyst is azobisisobutyronitrile (AIBN) in the absence of a solvent used at reaction temperatures of 50° to 75° C. Suitable styrenes include styrene, vinyl toluene, chlorostyrene, alphamethylstyrene and the like. Suitable alkenylphenyl esters include p-isopropenylphenyl acetate, p-isopropenylphenyl propionate, m-vinylphenyl acetate, methyl-p-isopropenylphenyl acetate and the like.

The partial or total hydrolysis of the copolymer of a styrene and an alkenylphenyl ester can be performed in the presence of less than stoichiometric or stoichiometric to greater than stoichiometric aqueous inorganic base, respectively. Inert organic solvents and phase transfer catalysts can optionally be utilized in the hydrolysis. Suitable inorganic bases include sodium hydroxide, potassium hydroxide and the like. Suitable inert organic solvents which can optionally be used include benzene, toluene, methylene chloride, methanol and the like. Suitable phase transfer catalysts which can optionally be used include benzyltrimethylammonium chloride, tetramethylphosphonium chloride and the like. Washing of the hydrolyzed copolymer with aqueous inorganic acid neutralizes any phenate groups within the copolymer chains. Suitable aqueous inorganic acids include hydrochloric acid and the like. The progress of the hydrolysis can conveniently be followed by infrared spectrophotometry.

The aromatic polycyanates optionally employed herein which are represented by formula II can be prepared using methods taught by U.S. Pat. No. 4,094,852; German Pat. No. 1,190,184 or the methods described herein.

The epoxy resins optionally employed herein which are represented by formulas III and IV can be prepared using methods taught by Lee and Neville in Handbook of Epoxy Resins (1967) published by McGraw-Hill Book Company.

The compositions of the present invention may be cured (polymerized) by heating from 70° to 350° C. or more, preferably by heating from 70° to 200° C. in the presence of 0.001 to 5 percent of a suitable catalyst. Operable catalysts include those taught by U.S. Pat. No. 4,094,852. Most preferred catalysts are cobalt naphthenate and cobalt octoate. Prepolymerization (B-staging) of the compositions of the present invention may be affected by using lower cure temperatures and/or shorter curing times. Curing of the prepolymerized resin may then be completed at a later time or immediately following prepolymerization to comprise a single curing step.

The compositions represented by formula I or by formulas I and II taken together polymerize through the formation of triazine structures to provide cured products. The progress of the polymerization can conveniently be followed by infrared spectrophotometry.

The compositions represented by formulae I (or formulas I and II taken together) and II and/or IV taken together polymerize through the formation of both triazine and oxazoline structures to provide cured products.

The compositions of the present invention are useful in the preparation of castings, laminates, coatings and the like.

The following examples are illustrative of the invention but are not to be construed as to limiting the scope thereof in any manner.

EXAMPLE 1

A. Preparation of p-Isopropenylphenyl Acetate and Styrene Copolymer 1543.0 grams of styrene and 95.7 grams of p-isopropenylphenyl acetate (5.83 percent by weight) and 1.64 grams of azobisisobutyronitrile catalyst (0.10 percent by weight) were added to a cylinderical glass reactor and maintained under a nitrogen atmosphere.

The p-isopropenylphenyl acetate used herein was in excess of 99 percent purity. Stirring at 3 rpm was started using a stainless steel auger capable of mixing very thick copolymer gel. Heating commenced and was maintained at 60° C. for 27.5 hours, after which time a highly viscous transparent copolymer gel had formed. The reaction was quenched by addition of methylene chloride containing 1 percent methanol (600 grams). The copolymer was dissolved in methylene chloride and reprecipitated with methanol. The copolymer suspended in the solvents was removed by filtration and vacuum dried at 100° C. for 24 hours (86,400 s). A total of 1005 grams of white-colored, fibrous copolymer was recovered. Gel permeation chromatography using polystyrene standards demonstrated an average molecular weight of 141,000 with a polydispersity ratio of 1.37. Infrared spectrophotometric analysis of a film of the copolymer confirmed the presence of the acetate carbonyl group absorbance. Nuclear magnetic resonance spectroscopy demonstrated a concentration of 6.1 percent by weight p-isopropenylphenyl acetate groups in the copolymer.

B. Hydrolysis of p-Isopropenylphenyl Acetate and Styrene Copolymer

An 200 gram portion of the p-isopropenylphenyl acetate and styrene copolymer, 850 grams of methanol, 200 grams of toluene, 2.0 milliliters of 60% aqueous benzytrimethylammonium chloride, and aqueous sodium hydroxide solution prepared from 50 grams of sodium hydroxide and 150 grams of water were added to a reactor and maintained under a nitrogen atmosphere with stirring. The reaction mixture was heated to a 72° C. reflux and maintained therein for 3.25 hours (11700 s), after which time the agglomerated copolymer was recovered by decantation of the reactor contents. At this time, infrared spectrophotometric analysis of an acid-washed film of the copolymer confirmed that complete hydrolysis had occurred as indicated by the disappearance of acetate carbonyl group absorbance and the appearance of phenolic hydroxyl group absorbance. The copolymer was dissolved in methylene chloride, washed with 500 grams 5 percent aqueous hydrochloric acid, then reprecipitated with methanol. The copolymer suspended in the solvents was removed by filtration and vacuum dried at 60° C. for 72 hours (259,200 s) to provide a white-colored, fibrous product.

C. Preparation of Polymeric Cyanate

An 88.0 gram portion of the hydrolyzed p-isopropenylphenyl acetate and styrene copolymer and 600 grams of chloroform were added to a reactor and maintained under a nitrogen atmosphere with stirring. The transparent viscous solution was coold to 0° C., then 34.96 grams of cyanogen bromide (0.30 mole) was added. Thirteen minutes (780 s) later, 34.96 grams of triethylamine (0.33 mole) was added to the reactor over a 31 minute (1860 s) period and so as to maintain the reaction temperature at $-1°$ to 2° C. After completion of triethylamine addition, the reactor was maintained at 2° to 5° C. for an additional 30 minutes (1800 s), followed by addition of 1000 milliliters of chilled water to the reactor. After 15 minutes (900 s), the water and chloroform plus product layers were separated. The chloroform plus product layer was washed with 500 milliliters 5 percent aqueous hydrochloric acid and then dried over anhydrous sodium sulfate. Filtration provided a dry chloroform solution of cyanate of hydrolyzed p-isopropenylphenyl acetate and styrene copolymer. Infrared spectrophotometric analysis confirmed the product structure as indicated by the disappearance of phenolic hydroxyl group absorbance of the appearance of cyanate group absorbance.

COMPARATIVE EXPERIMENT A—Preparation of Bisphenol A Dicyanate

A quantity of 222.45 grams of cyanogen bromide (2.10 moles) was added to a reactor containing 350 milliliters of stirred acetone under a nitrogen atmosphere. The cyanogen bromide-acetone solution was colled to $-15°$ C., then 228.30 grams of Bisphenol A (1.00 mole) dissolved in 700 milliliters of chilled acetone was added to the reactor. The stirred solution was allowed to equilibrate at $-5°$ C., then 203.39 grams of triethylamine (2.01 moles) was added to the reactor over a 125 minute (7500 s) period and so as to maintain the reaction temperature at $-5°$ C. After completion of the triethylamine addition, the reactor was maintained at $-5°$ C. for 30 minutes (1800 s), followed by addition of the reaction product to 650 milliliters of chilled water with agitation. After 15 minutes (900 s), the water and product mixture was multiply extracted with methylene chloride. The combined methylene chloride extracts were sequentially washed with dilute 5 percent hydrochloric acid, water, dilute hydrochloric acid, water and then dried over anhydrous magnesium sulfate. The dry methylene chloride extract was filtered and solvent removed by rotary evaporation under vacuum. Bisphenol A dicyanate, 255.0 grams, was recovered in 91.6 percent yield as a white crystalline solid. Infrared spectrophotometric analysis confirmed the product structure.

EXAMPLE 2

A pair of 12 in. × 12 in. (30.48 cm × 30.48 cm) woven fiberglass cloth pieces were equally impregnated with a solution prepared from 10.0 grams of the polymeric cyanate of Example 1C, 40.0 grams of Bisphenol A dicyanate of Comparative Experiment A, 166 grams of chloroform, 80 grams of methylene chloride and 0.166 gram of cobalt naphthenate (6.0 percent active). The fiberglass cloth used was a commercial-grade product treated with a proprietary coupling agent (Burlington 76-28 electrical laminating cloth) and had an average weight of 0.14 gram per square inch (0.0217 g/cm$^2$). The pair of impregnated fiberglass cloths were allowed to dry for 24 hours (86400 s) at room temperature (25° C.) followed by prepolymerization (B-staging) in a vented, forced-air, convection-type oven for 10 minutes (600 s) at 70° C., 15 minutes (900 s) at 100° C., then 15 minutes (900 s) at 150° C. Each cloth was cooled, found to be tack-free at room temperature and then cut to provide eight 6 in. × 6 in. (15.24 cm × 15.24 cm) pieces. The pieces were stacked into a 6 in. × 6 in. × 1/16 in. (15.24 cm × 15.24 cm × 0.15875 cm) stainless steel frame and placed between stainless steel plates which had been coated with a silicone mold release. The plates were loaded into a 150° C. hot press (Pasadena Hydraulics, Inc., Model P-215) and maintained for 10 minutes (600 s) at 100 psi (689.48 kPa), 5 minutes (300 s) at 400 psi (2758 kPa), then 10 minutes (600 s) at 1000 psi (6895 kPa). The temperature was then increased to 177° C. and this temperature was maintained for 1.0 hour (3600 s) at 5000 psi (34.5 MPa). After this time a 6 in. × 6 in. × 1/16 in. (15.24 cm × 15.24 cm × 0.15875 cm) light blue-colored, semi-transparent, rigid laminate was recovered and cut to provide a set of three 1 in. × 3 in. × 1/16 in. (2.54 cm × 7.62 cm × 0.15875 cm) flexural strength test pieces. The flexural strength test pieces were post-cured at 200° C. for 2 hours (7200 s) and then tested on an Instron machine with standard methods (ASTM D-790 modified). The Instron machine was set at a 2 in. (5.08 cm) span, 0.05 in. per minute (0.0021166 cm/s) crosshead speed and a 0.5 in. per minute (0.21166 cm/s) chart speed. The Barcol hardness value is on the 934-1 scale. The results are reported in Table I.

COMPARATIVE EXPERIMENT B

A pair of 12 in. × 12 in. (30.48 cm × 30.48 cm) woven fiberglass cloth pieces were equally impregnated with a solution prepared from 50.0 grams of Bisphenol A dicyanate of Comparative Experiment A, 100 grams of methylene chloride and 0.166 grams of cobalt naphthenate (6.0 percent active). Prepolymerization (B-staging), post-curing, laminate fabrication and mechanical property testing were completed using the method of Example 2, with the single exception that prepolymerization at the 150° C. temperature was increased to 20 minutes (1200 s) to provide a tack-free cloth at room temperature. Pressing at 150° C. was performed for 10 minutes (600 s) at 100 psi (689.5 kPa), 5 minutes (300 s) at 2000 psi (13.8 MPa), then 10 minutes (600 s) at 5000 psi (34.5 MPa). The temperature was then increased to 177° C. and this temperature was maintained for 1 hour (3600 s) with the 5000 psi (34.5 MPa). The laminate thus obtained was rigid, light amber-colored and semi-transparent. The resulrts are reported in Table I.

TABLE I

|  | Example 2 | Comparative Experiment B |
|---|---|---|
| Barcol Hardness | 54 | 54 |
| Flexural Strength, psi | $37.8 \times 10^3$ | $49.3 \times 10^3$ |
| kPa | $260.6 \times 10^3$ | $339.9 \times 10^3$ |
| Flexural Modulus, psi | $2.98 \times 10^6$ | $2.74 \times 10^6$ |
| kPa | $20.55 \times 10^6$ | $18.89 \times 10^6$ |

EXAMPLE 3

A 1/16 in. (0.15875 cm) laminate was prepared using the method of Example 2. Flexural strength test pieces, 1 in. × 2 in. × 1/16 in. (2.54 cm × 5.08 cm. × 0.15875 cm) were tested on an Instron machine with standard methods (ASTM D-790). The Instron machine was set at a 1 in. (2.54 cm) span, 0.02 in. per minute (0.0008466 cm/s) crosshead speed and a 0.5 in. per minute (0.021 cm/s) chart speed. The flexural strength thus obtained was $60.4 \times 10^3$ psi ($416.4 \times 10^3$ kPa) and the flexural modulus was $3.48 \times 10^6$ psi ($24 \times 10^6$ kPa).

EXAMPLE 4

A pair of 12 in. × 12 in. (30.48 cm × 30.48 cm) woven fiberglass cloth pieces were equally impregnated with a solution prepared from 35.45 grams of the polymeric cyanate of Example 1C, 14.54 grams of the diglycidyl ether of Bisphenol A having an epoxide equivalent weight (EEW) of 183, 467.22 grams of chloroform, and 0.166 grams of cobalt naphthenate (6.0 percent active). The fiberglass cloth used was a commercial-grade product treated with a proprietary coupling agent (Burlington 76-28 electrical laminating cloth) and had an average weight of 0.14 gram per square inch (0.0217 g/cm²). The pair of impregnated fiberglass cloths were allowed to dry for 24 hours (86400 s) at room temperature (25° C.) followed by prepolymerization (B-staging) in a vented, forced air, convection-type oven for twenty-five minutes (1500 s) at 70° C. Each cloth was cooled, found to be tack-free at room temperature and then cut to provide eight 6 in. × 6 in. (15.24 cm × 15.24 cm) pieces. The pieces were stacked into a 6 in. × 6 in. × 1/16 in. (15.24 cm × 15.24 cm × 0.15875 cm) stainless steel frame and placed between stainless steel plates which had been coated with a silicone mold release. The plates were loaded into a 150° C. hot press (Pasadena Hydraulics Inc., Model P-215) and maintained for 5 minutes (300 s) at 500 psi (3.445 MPa), then 5 minutes (300 s) at 5000 psi (34.5 MPa). The temperature was then increased to 177° C. and this temperature was maintained for 1 hour (3600 s) at 5000 psi (34.5 MPa). After this time, a 6 in. × 6 in. × 1/16 in. (15.24 cm × 15.24 cm × 0.15875 cm) light amber-colored, transparent, rigid laminate was recovered and cut to provide a set of three 1 in. × 3 in. × 1/16 in. (2.54 cm × 7.62 cm × 0.15875 cm) flexural strength test pieces. Post-curing and mechanical property testing was completed using the method of Example 2. The results are reported in Table II.

TABLE II

| Barcol Hardness | 54 |
|---|---|
| Flexural Strength, psi | $41.7 \times 10^3$ |
| kPa | $287.5 \times 10^3$ |
| Flexural Modulus, psi | $25.9 \times 10^6$ |
| kPa | $178.6 \times 10^6$ |

EXAMPLE 5

A 70.5 gram portion of the hydrolyzed p-isopropenylphenyl acetate and styrene copolymer from Example 1B, 580 grams of chloroform, 28.16 grams of cyanogen bromide (0.0266 mole), and 24.45 grams of triethylamine (0.242 mole) were used to prepare a polymeric cyanate using the method of Example 1C. A pair of 12 in. × 12 in. (30.48 cm × 30.48 cm) woven fiberglass cloth pieces were equally impregnated with a solution prepared from a 25.0 gram portion of the polymeric cyanate, 25.0 grams of Bisphenol A dicyanate of Comparative Experiment A, 544 grams of chloroform, 25 grams of methylene chloride and 0.166 gram of cobalt naphthenate (6.0 percent active). The fiberglass cloth used was a commercial-grade product treated with a proprietary coupling agent (Burlington 76-28 electrical laminating cloth) and had an average weight of 0.14 gram per square inch (0.0021277 kPa). The pair of impregnated fiberglass cloths were allowed to dry for 24 hours (86400 s) at room temperature (25° C.) followed by prepolymerization (B-staging) in a vented, forced-air, convection-type oven for 45 minutes at 70° C., 5 minutes (300 s) at 100° C., then 10 minutes (600 s) at 150° C. Each cloth was cooled, found to be tack-free at room temperature and then cut to provide eight 6 in. × 6 in. (15.24 cm × 15.24 cm) pieces. The pieces were stacked into a 6 in. × 6 in. × 1/16 in. (15.24 cm × 15.24 cm × 0.15875 cm) stainless steel frame and placed between stainless steel plates which had been coated with a silicone mold release. The plates were loaded into a 200° C. hot press (Pasadena Hydraulics Inc., Model P-215) and maintained for 1 hour (3600 s) at 5000 psi (34.5 MPa). After this time a 6 in. × 6 in. × 1/16 in. (15.24 cm × 15.24 cm × 0.15875 cm) light amber colored, transparent, rigid laminate was recovered and cut to provide a set of three 1 in.×3 in.×1/16 in. (2.54 cm×7.62 cm×0.15875 cm) flexural strength test pieces. Post-curing and mechanical property testing was completed using the method of Example 2. The results are reported in Table III.

TABLE III

| Barcol Hardness | 55 |
|---|---|
| Flexural Strength, psi | 46.4 × 10³ |
| kPa | 319.9 × 10³ |
| Flexural Modulus, psi | 2.60 × 10⁶ |
| kPa | 17.9 × 10⁶ | laminate test piece was weighed, then all were immersed under water and maintained therein for 10 days (864,000 s) at a temperature of 25° C. On the fourth day (346,000 s) of exposure to the water, the test pieces were removed, blotted, weighed, and then replaced back into the water. After 10 days (864,000 s) of exposure, the test pieces were removed and again weighed. All test pieces were kept moist just prior to testing on an Instron machine using the method of Example 2. The results are reported in Table V where comparisons against the unexposed (initial) properties are also provided.

TABLE V

|  | Example 2 | Example 4 | Example 5 | Comparative Experiment B |
|---|---|---|---|---|
| Barcol Hardness | | | | |
| initial | 41 | 54 | 55 | 54 |
| exposed | 44 | 54 | 55 | 41 |
| (percent change) | (+7.32) | (0) | (0) | (−24.07) |
| Flexural Strength | | | | |
| initial, psi | 36.2 × 10³ | 41.7 × 10³ | 46.4 × 10³ | 49.3 × 10³ |
| kPa | 249.6 × 10³ | 287.5 × 10³ | 320 × 10³ | 340 × 10³ |
| exposed, psi | 36.0 × 10³ | 42.6 × 10³ | 43.5 × 10³ | 42.1 × 10³ |
| kPa | 248.2 × 10³ | 293.7 × 10³ | 300 × 10³ | 290.3 × 10³ |
| (percent change) | (−0.55) | (+2.16) | (−6.25) | (−14.60) |
| Flexural Modulus | | | | |
| initial, psi | 2.92 × 10⁶ | 2.59 × 10⁶ | 2.60 × 10⁶ | 2.74 × 10⁶ |
| kPa | 20.13 × 10⁶ | 17.86 × 10⁶ | 17.93 × 10⁶ | 18.89 × 10⁶ |
| exposed, psi | 2.96 × 10⁶ | 2.74 × 10⁶ | 2.51 × 10⁶ | 2.70 × 10⁶ |
| kPa | 20.41 × 10⁶ | 18.89 × 10⁶ | 17.31 × 10⁶ | 18.62 × 10⁶ |
| (percent change) | (+1.37) | (+5.79) | (−3.46) | (−1.46) |
| Percent Weight Gain | | | | |
| 4 days of exposure | 0.61 | 0.16 | 0.19 | 0.83 |
| 10 days of exposure | 0.67 | 0.22 | 0.28 | 1.53 |

EXAMPLE 6

The solutions of Example 2 and Comparative Experiment B were each prepared. A one gram sample of each solution was devolatilized to remove solvent then cured at 177° C. for 1 hour (3600 s) and 200° C. for 2 hours (7200 s). A portion of each cured polytriazine product was used for thermal gravimetric analysis (TGA). The lower temperature limit was 50° C. while the upper temperature limit was 950° C. A heating rate of 50° C. per minute (0.83° C./s) was used. All analysis was performed under a nitrogen atmosphere. The results are reported in Table IV.

TABLE IV

| | Percent of Original Weight | |
|---|---|---|
| Temperature (°C.) | Example 2 | Comparative Experiment B |
| 400 | 96.7 | 99.6 |
| 450 | 85.5 | 93.8 |
| 500 | 54.5 | 59.8 |
| 550 | 48.0 | 50.8 |
| 600 | 43.1 | 45.9 |
| 650 | 40.7 | 42.6 |
| 700 | 38.8 | 39.3 |
| 750 | 37.8 | 35.8 |
| 800 | 37.1 | 31.9 |
| 850 | 36.4 | 28.1 |
| 900 | 36.2 | 24.5 |
| 950 | 36.2 | 21.2 |

EXAMPLE 7

A set of three 1 in.×3 in.×1/16 in. (2.54 cm×7.62 cm×0.15875 cm) flexural strength test pieces were cut from the laminates of Example 2, Example 4, Example 5 and Comparative Experiment B, respectively, and then post-cured at 200° C. for 2 hours (7200 s). Each

I claim:
1. A composition which comprises
(A) from about 1 to 100 percent by weight (pbw) of a polymeric cyanate or mixture of polymeric cyanates represented by the formula

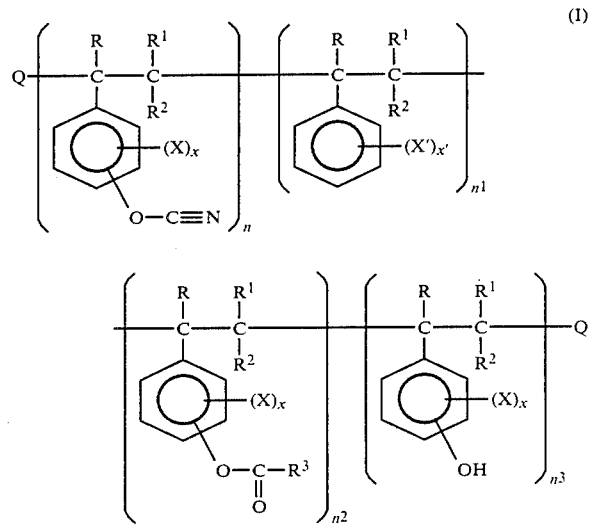

wherein each R, R¹ and R² is independently hydrogen or an alkyl group having from 1 to about 3 carbon atoms; R³ is an alkyl group having from 1 to about 3 carbon atoms; each X and X' is independently an alkyl group having from 1 to about 4 carbon atoms, chlorine or bromine; Q is independently a group derived from any suitable polymerization initiator or terminator, hydrogen,

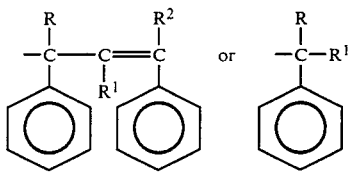

wherein each R, $R^1$, and $R^2$ is as defined above, and wherein each aromatic ring may contain any substituent group as those enumerated in the formula I; n has a value of from about 1 to about 5000; $n^1$ has a value from about 1 to about 5000; $n^2$ has a value of from about zero to about 1000; $n^3$ has a value from about zero to about 1000; and each x and x' independently has a value from zero to 4; and (B) from zero to about 99 pbw of an aromatic polycyanate or mixture of aromatic polycyanates represented by the formula:

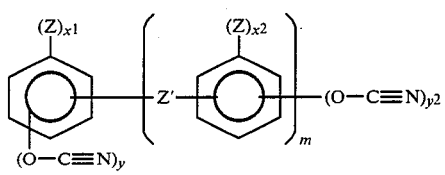
(II)

wherein each Z is independently hydrogen, an alkyl group having from 1 to about 4 carbon atoms, chlorine, bromine, or a

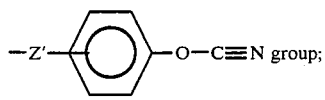 group;

Z' is a direct bond, an alkylene group with 1 to 5 carbon atoms, —S—, —S—S—, —O—,

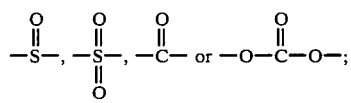

y has a value from zero to 5 when m has a value of 1 to 3; y has a value from 2 to 5 when m has a value of zero; $x^1$ has a value of 5 minus the value of y when m has a value of 1 to 3; $x^1$ has a value of 6 minus the value of y plus $y^2$ when m has a value of zero; $x^2$ has a value of 5 minus the value of $y^2$; $y^2$ has a value of zero to 5; m has a value of zero to 3; with the proviso that the sum of y and $y^2$ is always at least two; and (C) from zero to about 99 pbw of an epoxy resin or mixture of epoxy resins represented by the formulas

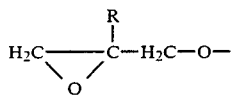
III

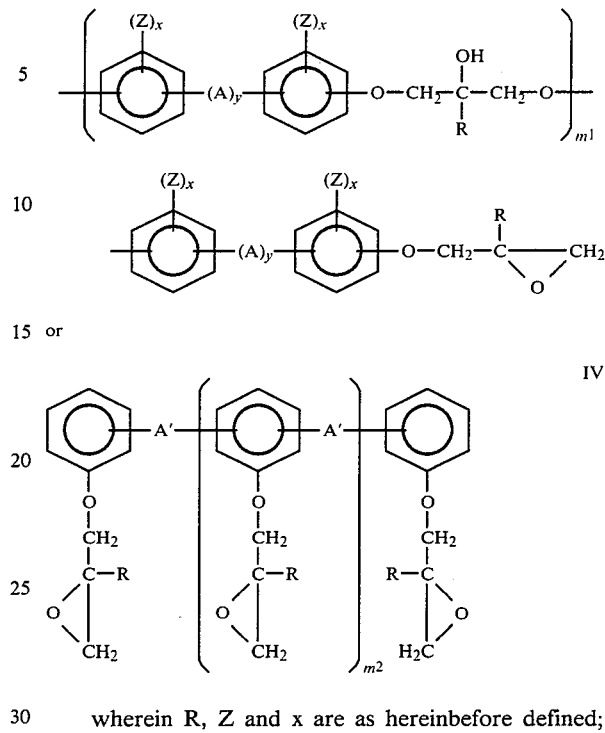

wherein R, Z and x are as hereinbefore defined; each A is independently a hydrocarbyl group having from 1 to about 10 carbon atoms, —S—, —S—S—, —O—,

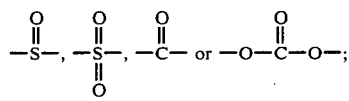

each A' is independently a hydrocarbyl group having from 1 to about 10 carbon atoms, each y independently has a value of zero or 1; $m^1$ has a value of zero to about 99; $m^2$ has a value of 1 to 10 and wherein the pbw of the individual components is based upon total composition.

2. A composition of claim 1 wherein
(a) component (A) is present in a quantity of from about 1 to about 80 pbw;
(b) component (B) is present in a quantity of from about 5 to about 70 pbw;
(c) component (C) is present in a quantity of from one to about 50 pbw; and
(d) in component (A), n has a value of from about 10 to about 2500; $n^1$ has a value of from about 100 to about 3000; and $n^2$ and $n^3$ have a value of about zero.

3. A composition of claim 2 wherein
(a) component (A) is present in a quantity of from about 10 to about 50 pbw;
(b) component (B) is present in a quantity of from about 25 to about 50 pbw; and
(c) component (C) is present in a quantity of from about 5 to about 25 pbw.

4. A composition of claim 1 wherein components (B) and (C) are not present.

5. A composition of claim 1 wherein component (B) is not present, component (A) is present in a quantity of from about 1 to about 99 pbw and component (C) is present in a quantity of from about 1 to about 99 pbw.

6. A composition of claim 1 wherein component (C) is not present, component (A) is present in a quantity of from about 1 to about 99 pbw and component (B) is present in a quantity of from about 1 to about 99 pbw.

7. A composition of claim 2 wherein each R is independently methyl or hydrogen, each $R^1$ and $R^2$ are hydrogen and x is zero.

8. A composition of claim 3 wherein each R is independently methyl or hydrogen, each $R^1$ and $R^2$ are hydrogen and x is zero.

9. A composition of claim 4 wherein each R is independently methyl or hydrogen, each $R^1$ and $R^2$ are hydrogen and x is zero.

10. A composition of claim 5 wherein each R is independently methyl or hydrogen, each $R^1$ and $R^2$ are hydrogen and x is zero.

11. A composition of claim 6 wherein each R is independently methyl or hydrogen, each $R^1$ and $R^2$ are hydrogen and x is zero.

12. A composition of claim 2 wherein each R is independently methyl or hydrogen, each $R^1$ and $R^2$ are hydrogen, each X is chlorine or bromine and each x has a value such that there is an average of about 1 chlorine or bromine atom on each ring.

13. A composition of claim 3 wherein each R is independently methyl or hydrogen, each $R^1$ and $R^2$ are hydrogen, each X is chlorine or bromine and each x has a value such that there is an average of about 1 chlorine or bromine atom on each ring.

14. A composition of claim 4 wherein each R is independently methyl or hydrogen, each $R^1$ and $R^2$ are hydrogen, each X is chlorine or bromine and each x has a value such that there is an average of about 1 chlorine or bromine atom on each ring.

15. A composition of claim 5 wherein each R is independently methyl or hydrogen, each $R^1$ and $R^2$ are hydrogen, each X is chlorine or bromine and each x has a value such that there is an average of about 1 chlorine or bromine atom on each ring.

16. A composition of claim 6 wherein each R is independently methyl or hydrogen, each $R^1$ and $R^2$ are hydrogen, each X is chlorine or bromine and each x has a value such that there is an average of about 1 chlorine or bromine atom on each ring.

17. A composition of claim 6 wherein component (C) is an epoxy resin or mixture of epoxy resins represented by formula III.

18. A composition of claim 16 wherein component (C) is an epoxy resin or mixture of epoxy resins represented by formula III.

19. A composition of claim 2 wherein each R is independently methyl or hydrogen, each $R^1$ and $R^2$ are hydrogen, each X is hydrogen or an alkyl group having from 1 to about 4 carbon atoms, each X' is chlorine or bromine and each x' has a value such that there is an average of about 1 chlorine or bromine atom on each ring defined by $n^1$.

20. A composition of claim 3 wherein each R is independently methyl or hydrogen, each $R^1$ and $R^2$ are hydrogen, each X is hydrogen or an alkyl group having from 1 to about 4 carbon atoms, each X' is chlorine or bromine and each x' has a value such that there is an average of about 1 chlorine or bromine atom on each ring defined by $n^1$.

21. A composition of claim 4 wherein each R is independently methyl or hydrogen, each $R^1$ and $R^2$ are hydrogen, each X is hydrogen or an alkyl group having from 1 to about 4 carbon atoms, each X' is chlorine or bromine and each x' has a value such that there is an average of about 1 chlorine or bromine atom on each ring defined by $n^1$.

22. A composition of claim 5 wherein each R is independently methyl or hydrogen, each $R^1$ and $R^2$ are hydrogen, each X is hydrogen or an alkyl group having from 1 to about 4 carbon atoms, each X' is chlorine or bromine and each x' has a value such that there is an average of about 1 chlorine or bromine atom on each ring defined by $n^1$.

23. A composition of claim 6 wherein each R is independently methyl or hydrogen, each $R^1$ and $R^2$ are hydrogen, each X is hydrogen or an alkyl group having from 1 to about 4 carbon atoms, each X' is chlorine or bromine and each x' has a value such that there is an average of about 1 chlorine or bromine atom on each ring defined by $n^1$.

24. A product resulting from mixing a composition of claim 1 with an effective quantity of a suitable curing agent or catalyst or mixture of such curing agents or catalysts and subjecting the mixture to curing conditions.

25. A product resulting from mixing a composition of claim 2 with an effective quantity of a suitable curing agent or catalyst or mixture of such curing agents or catalysts and subjecting the mixture to curing conditions.

26. A product resulting from mixing a composition of claim 3 with an effective quantity of a suitable curing agent or catalyst or mixture of such curing agents or catalysts and subjecting the mixture to curing conditions.

27. A product resulting from mixing a composition of claim 4 with an effective quantity of a suitable curing agent or catalyst or mixture of such curing agents or catalysts and subjecting the mixture to curing conditions.

28. A product resulting from mixing a composition of claim 5 with an effective quantity of a suitable curing agent or catalyst or mixture of such curing agents or catalysts and subjecting the mixture to curing conditions.

29. A product resulting from mixing a composition of claim 6 with an effective quantity of a suitable curing agent or catalyst or mixture of such curing agents or catalysts and subjecting the mixture to curing conditions.

30. A product resulting from mixing a composition of claim 7 with an effective quantity of a suitable curing agent or catalyst or mixture of such curing agents or catalysts and subjecting the mixture to curing conditions.

31. A product resulting from mixing a composition of claim 8 with an effective quantity of a suitable curing agent or catalyst or mixture of such curing agents or catalysts and subjecting the mixture to curing conditions.

32. A product resulting from mixing a composition of claim 9 with an effective quantity of a suitable curing agent or catalyst or mixture of such curing agents or catalysts and subjecting the mixture to curing conditions.

33. A product resulting from mixing a composition of claim 10 with an effective quantity of a suitable curing agent or catalyst or mixture of such curing agents or catalysts and subjecting the mixture to curing conditions.

34. A product resulting from mixing a composition of claim 11 with an effective quantity of a suitable curing agent or catalyst or mixture of such curing agents or catalysts and subjecting the mixture to curing conditions.

35. A product resulting from mixing a composition of claim 12 with an effective quantity of a suitable curing agent or catalyst or mixture of such curing agents or catalysts and subjecting the mixture to curing conditions.

36. A product resulting from mixing a composition of claim 13 with an effective quantity of a suitable curing agent or catalyst or mixture of such curing agents or catalysts and subjecting the mixture to curing conditions.

37. A product resulting from mixing a composition of claim 14 with an effective quantity of a suitable curing agent or catalyst or mixture of such curing agents or catalysts and subjecting the mixture to curing conditions.

38. A product resulting from mixing a composition of claim 15 with an effective quantity of a suitable curing agent or catalyst or mixture of such curing agents or catalysts and subjecting the mixture to curing conditions.

39. A product resulting from mixing a composition of claim 16 with an effective quantity of a suitable curing agent or catalyst or mixture of such curing agents or catalysts and subjecting the mixture to curing conditions.

40. A product resulting from mixing a composition of claim 17 with an effective quantity of a suitable curing agent or catalyst or mixture of such curing agents or catalysts and subjecting the mixture to curing conditions.

41. A product resulting from mixing a composition of claim 18 with an effective quantity of a suitable curing agent or catalyst or mixture of such curing agents or catalysts and subjecting the mixture to curing conditions.

42. A product resulting from mixing a composition of claim 19 with an effective quantity of a suitable curing agent or catalyst or mixture of such curing agents or catalysts and subjecting the mixture to curing conditions.

43. A product resulting from mixing a composition of claim 20 with an effective quantity of a suitable curing agent or catalyst or mixture of such curing agents or catalysts and subjecting the mixture to curing conditions.

44. A product resulting from mixing a composition of claim 21 with an effective quantity of a suitable curing agent or catalyst or mixture of such curing agents or catalysts and subjecting the mixture to curing conditions.

45. A product resulting from mixing a composition of claim 22 with an effective quantity of a suitable curing agent or catalyst or mixture of such curing agents or catalysts and subjecting the mixture to curing conditions.

46. A product resulting from mixing a composition of claim 23 with an effective quantity of a suitable curing agent or catalyst or mixture of such curing agents or catalysts and subjecting the mixture to curing conditions.

\* \* \* \* \*